(12) United States Patent
Ono et al.

(10) Patent No.: US 8,752,962 B2
(45) Date of Patent: Jun. 17, 2014

(54) OPHTHALMIC APPARATUS

(75) Inventors: Shigeaki Ono, Tokyo (JP); Masao Shikaumi, Tokyo (JP); Kyoji Sekiguchi, Utsunomiya (JP); Koji Uchida, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 776 days.

(21) Appl. No.: 12/831,137

(22) Filed: Jul. 6, 2010

(65) Prior Publication Data

US 2011/0007274 A1    Jan. 13, 2011

(30) Foreign Application Priority Data

Jul. 9, 2009    (JP) ................................. 2009-162825

(51) Int. Cl.
*A61B 3/10* (2006.01)
*A61B 3/14* (2006.01)
*A61B 3/12* (2006.01)
*A61B 3/00* (2006.01)

(52) U.S. Cl.
CPC ............... *A61B 3/12* (2013.01); *A61B 3/0008* (2013.01); *A61B 3/14* (2013.01); *A61B 3/1225* (2013.01)
USPC ........................................ 351/206; 351/221

(58) Field of Classification Search
USPC ............................ 351/205, 206, 208, 213, 221
See application file for complete search history.

(56) References Cited

U.S. PATENT DOCUMENTS

| 5,572,266 | A | 11/1996 | Ohtsuka | |
|---|---|---|---|---|
| 2006/0126017 | A1* | 6/2006 | Mizuochi | 351/206 |
| 2012/0008093 | A1* | 1/2012 | Spaide | 351/206 |
| 2012/0038886 | A1* | 2/2012 | Dobashi et al. | 351/208 |
| 2012/0057128 | A1* | 3/2012 | Aikawa et al. | 351/206 |

FOREIGN PATENT DOCUMENTS

| JP | 62-034530 | A | | 2/1987 |
|---|---|---|---|---|
| JP | 7-031590 | A | | 2/1995 |
| JP | 09-131316 | A | | 5/1997 |
| JP | 09131316 | A | * | 5/1997 |

* cited by examiner

*Primary Examiner* — Mahidere Sahle
(74) *Attorney, Agent, or Firm* — Canon U.S.A., Inc., IP Division (57) ABSTRACT

When the fundus camera is positioned on the same side as the subject's eye relative to an appropriate position (front-focus state), the positioning index light source turned on in blue produces most-focused positioning index images. The positioning index light sources become more blurred in order of green and red. When the camera is positioned on the opposite side of the subject's eye relative to the appropriate position (rear-focus state), the positioning index light source turned on in red produces most-focused images. The positioning index light sources become more blurred in order of green and blue. Based on a degree of the blur of the individual positioning index images in red, green, and blue reflected by the cornea of the subject's eye, the calculation unit calculates whether to move the camera body closer to or farther away from the subject's eye and allows the display unit to display the information.

22 Claims, 13 Drawing Sheets

OPHTHALMIC APPARATUS

BACKGROUND OF THE INVENTION

1. Field of the Invention

The present invention relates to an ophthalmic apparatus capturing an image of or measuring a subject's eye.

2. Description of the Related Art

Japanese Patent Application Publication No. 62-34530 discusses a fundus camera projecting an alignment index on a cornea of a subject's eye and obtaining a reflected image from the cornea as an alignment image. According to this technique, whether the fundus camera is in an appropriate alignment position is determined based on the focus status of the alignment image.

Japanese Patent Application Publication No. 7-31590 also discusses a fundus camera projecting an alignment index on a cornea of a subject's eye and obtaining a reflected image from the cornea as an alignment image. According to this technique, whether the fundus camera is in an appropriate alignment position is determined based on separation or agreement of the alignment image.

Since the above fundus cameras use singly a single-wavelength light-emitting diode (LED) as a light source for the alignment index, they can determine whether the fundus camera is in an appropriate alignment position, to be sure. However, neither of the fundus cameras can determine whether the fundus camera is positioned close to or far from the subject's eye with respect to an appropriate alignment position. Namely, neither of the fundus cameras can accurately determine the working distance.

Thus, to determine an appropriate direction to move the fundus camera to an appropriate alignment position, the operator first needs to temporarily move the fundus camera closer to or farther away from the subject's eye and next needs to observe whether or not the blur level or the separation level of the alignment image has increased. It is not a problem if the operator moves the fundus camera in an appropriate direction in his/her first attempt. However, movement of the fundus camera in the opposite direction will result in a needless operation.

SUMMARY OF THE INVENTION

The present invention is directed to an ophthalmic apparatus capable of detecting an appropriate working distance from a subject's eye and successfully capturing an image of the subject's eye.

According to an aspect of the present invention, an ophthalmic apparatus includes: an illumination optical system configured to project illumination light on a fundus of a subject's eye; an imaging optical system configured to capture an image reflected from the fundus via an objective lens; an index projection unit configured to project a positioning index on a cornea of the subject's eye via the objective lens; an index imaging unit configured to capture an image reflected from the cornea on which the index projection unit projects the positioning index; a wavelength range selection unit configured to select at least two wavelength ranges among wavelength ranges of the index projection unit or wavelength ranges of the index imaging unit; a characteristics calculation unit configured to calculate characteristics of an index image captured by the index imaging unit; and a positional gap information detection unit configured to detect information about positional gap between the subject's eye and the imaging optical system relative to an appropriate working distance, based on the characteristics calculated by the characteristics calculation unit for each of the wavelength ranges selected by the wavelength range selection unit.

Based on the ophthalmic apparatus according to the present invention, by analyzing the size of the blur of each positioning index image, an appropriate direction in moving the apparatus body part relative to the subject's eye can be detected, and an image of the subject's eye can be successfully captured without undesired light such as flare and ghost.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
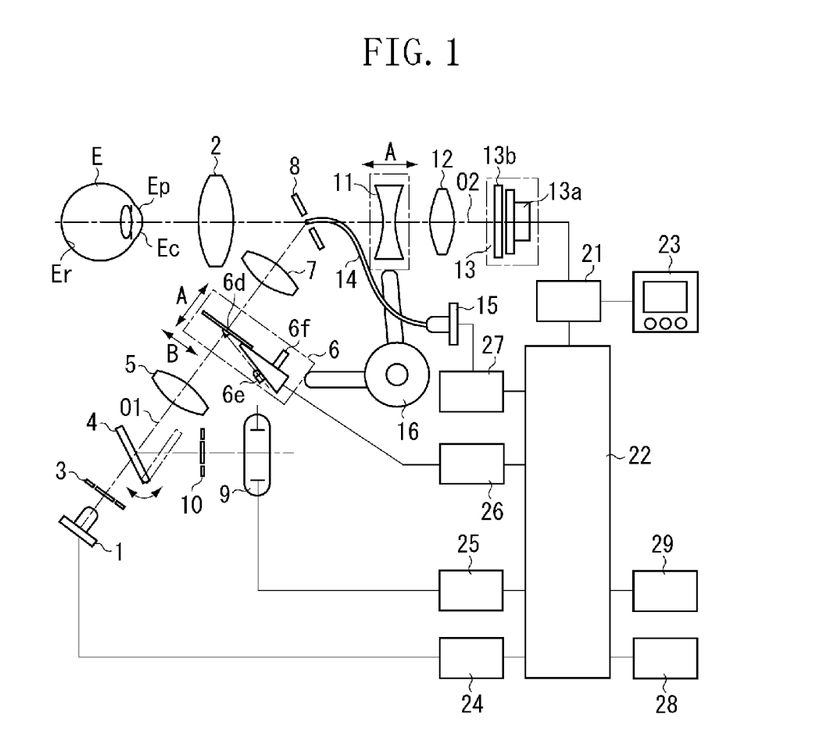
FIG. 1 illustrates a configuration of a fundus camera according to a first exemplary embodiment.

FIG. 1 illustrates a configuration of a fundus camera as an ophthalmic apparatus according to a first exemplary embodiment. The fundus camera includes an illumination optical system having an optical path O1 that runs from an observation light source 1 to an objective lens 2 facing a subject's eye E. The illumination optical system includes a diaphragm 3, a quick-return mirror 4, a relay lens 5, a focus index projection unit 6, a relay lens 7, and a perforated mirror 8 sequentially arranged in the optical path O1. When an operator observes a fundus, the quick-return mirror 4 retracts from the optical path O1 to a position indicated by a dashed line in FIG. 1. When the operator captures an image of the fundus, the quick-return mirror 4 is inserted to the optical path O1 in a position indicated by a solid line. The fundus camera further includes an imaging light source 9 and a diaphragm 10 arranged in a direction in which light emitted from the imaging light source 9 enters the quick-return mirror 4.

Figure 2:
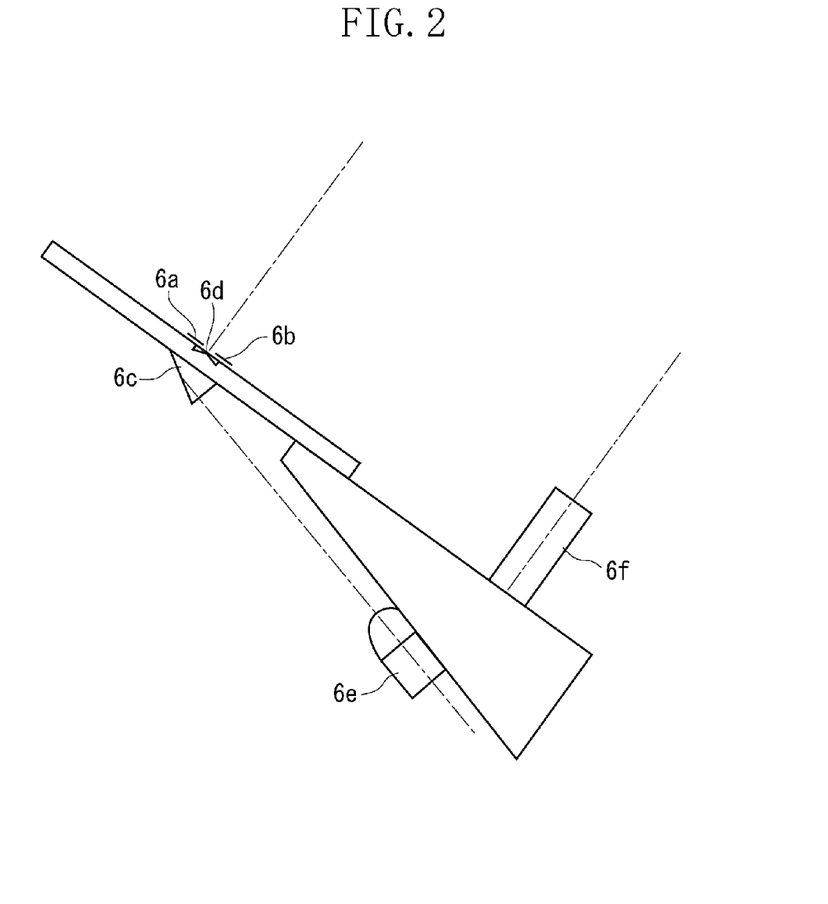
FIG. 2 illustrates a configuration of a focus index projection unit.

As illustrated in FIG. 2, the focus index projection unit 6 includes a focus split prism formed by prism units 6a, 6b, and 6c, a focus index 6d having a rectangular aperture, and a focus index light source 6e. The focus index light source 6e includes an LED having the center wavelength thereof in the visible light range. Further, the focus index projection unit 6 is rotatable around a shaft 6f and is retractable from the optical path O1.

Figure 3:
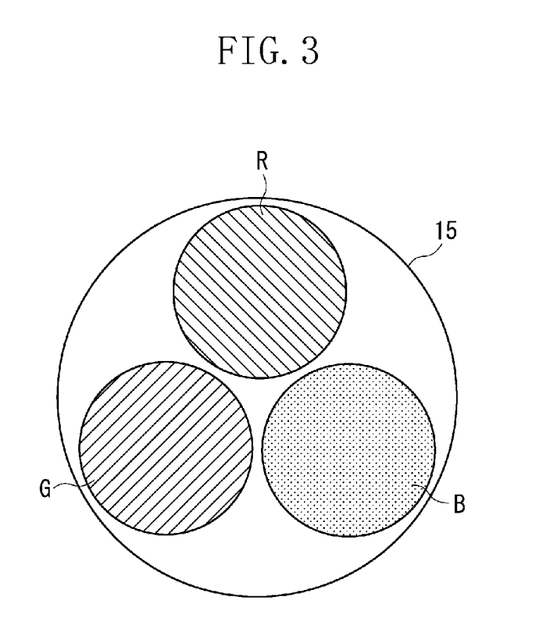
FIG. 3 is a front view of a positioning index light source seen from an optical fiber.

The fundus camera further includes an imaging optical system having an optical path O2 behind the perforated mirror 8. The imaging optical system includes a focusing lens 11, an imaging lens 12, and an imaging unit 13 including an image sensor 13a and a tricolor wavelength separation unit 13b. The imaging unit 13 captures images of a fundus and indexes. The fundus camera further includes an optical fiber 14 having an exit end in the aperture of the perforated mirror 8 and an entrance end connected to a positioning index light source 15. This positioning index light source 15 includes tricolor LEDs and can separately emit light of a wavelength of three colors red (R), green (G), and blue (B), as illustrated in FIG. 3.

A focus link mechanism 16 drives the focus index projection unit 6 in conjunction with the focusing lens 11 in direction A of FIG. 1. Namely, the focus index 6d of the focus index projection unit 6 and the image sensor 13a of the imaging unit 13 are optically brought in a conjugate relation with each other. When the operator captures a still image, the focus index projection unit 6 rotates around the shaft 6f and retracts from the optical path O1 in direction B of FIG. 1.

The image sensor 13a of the imaging unit 13 outputs a signal to a calculation unit 22 and a display unit 23 via an image signal processing unit 21. The calculation unit 22 outputs a signal to the observation light source 1, the imaging light source 9, the focus index projection unit 6, and the positioning index light source 15 via drive units 24 to 27, respectively. The calculation unit 22 is connected to an input unit 28 and a recording unit 29.

When the operator observes a fundus, the calculation unit 22 drives the drive unit 24 to turn on the observation light source 1 or to control the light amount emitted therefrom. The observation light source 1 includes a white LED having spectral sensitivity characteristics in almost all visible light ranges. A luminous flux emitted by the observation light source 1 passes through the diaphragm 3 having a ring aperture and next reaches the quick-return mirror 4. Since the quick-return mirror 4 is retracted from the optical path O1, the luminous flux passes through the relay lens 5, the focus index projection unit 6, and the relay lens 7. Reflected by the perforated mirror 8, the luminous flux passes through the objective lens 2 and a cornea Ec and a pupil Ep of the subject's eye E to illuminate a fundus Er. Simultaneously, the calculation unit 22 drives the drive circuit 26 to turn on the focus index light source 6e and project index images on the fundus Er with the focus index 6d.

The illuminated fundus Er reflects the luminous flux, which then passes through the pupil Ep, the cornea Ec, the objective lens 2, the aperture of the perforated mirror 8, the focusing lens 11, the imaging lens 12, and the tricolor wavelength separation unit 13b in the imaging unit 13. Next, the image sensor 13a receives the luminous flux and forms the fundus image and focus index images.

The calculation unit 22 also drives the drive circuit 27 to turn on the positioning index light source 15. The luminous flux emitted thereby passes through the optical fiber 14 and the objective lens 2 and illuminates the cornea Ec. The cornea Ec reflects the luminous flux, and while the image sensor 13a receives the luminous flux and forms positioning index images A, the positioning index images A are superimposed on the fundus image Er' and focus index images.

The image sensor 13a executes a photoelectric conversion for the fundus image Er', the focus index images, and the positioning index images A. After reading the converted signal data from the image sensor 13a, the image signal processing unit 21 amplifies the data and converts the amplified data from analog to digital to generate digital moving image data. The image signal processing unit 21 supplies the image data to the calculation unit 22 and the display unit 23 which simultaneously displays the image data.

Figure 4A:
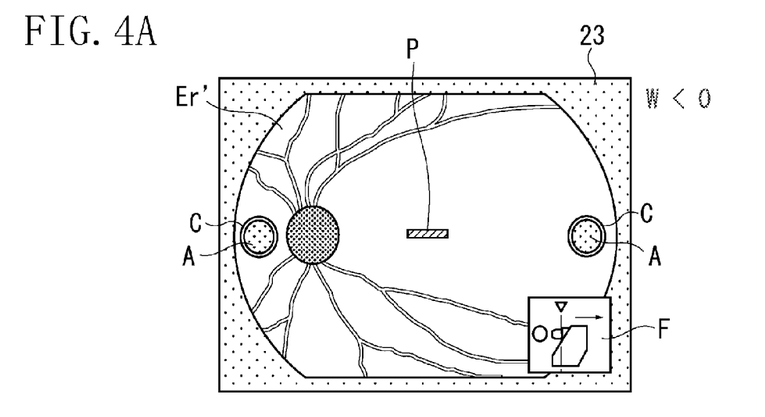
FIGS. 4A to 4C illustrate positional relationships between the fundus camera and a subject's eye.
Figure 4B:
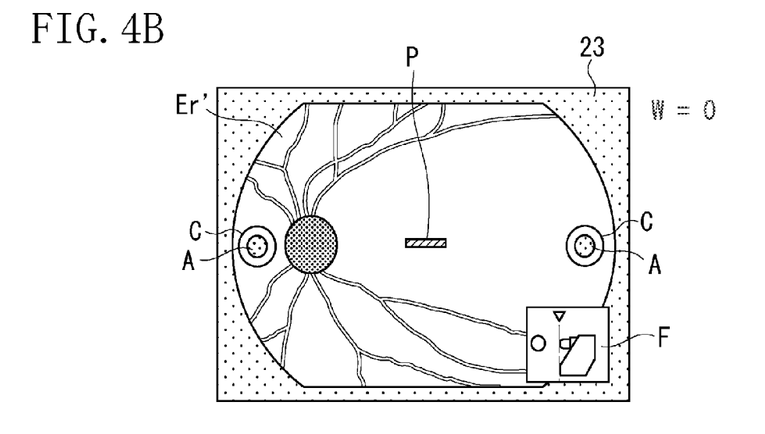
Figure 4C:
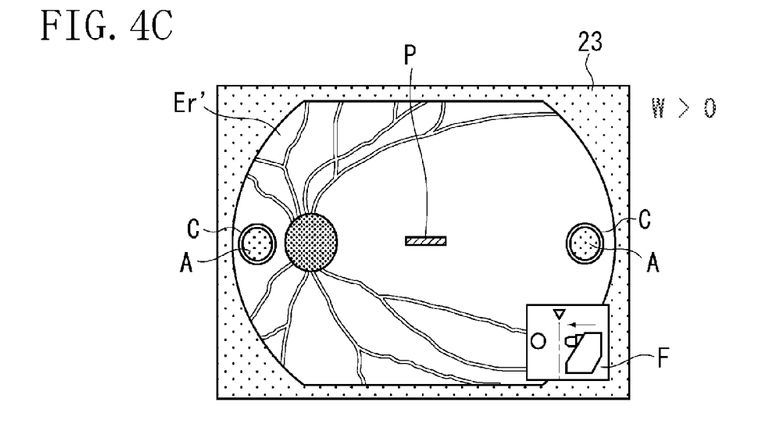

For the adjustment and positioning of the working distance, the operator moves the fundus camera vertically and/or horizontally, so that each of the positioning index images A is positioned in the center of a positioning index circle C in the fundus image Er' illustrated in FIGS. 4A to 4C. Assuming that the working distance between the current position of a fundus camera and an appropriate position of the fundus camera with respect to the subject's eye E is W in the optical path O2 of the imaging optical system, when the fundus camera is positioned on the same side as the subject's eye E with respect to the appropriate position as illustrated in FIG. 4A, the working distance is represented as W<0. In contrast, when the fundus camera is positioned on the opposite side of the subject's eye E with respect to the appropriate position as illustrated in FIG. 4C, the working distance is represented as W>0. Further, when the working distance is appropriate as illustrated in FIG. 4B, the working distance is represented as W=0.

Figure 5:
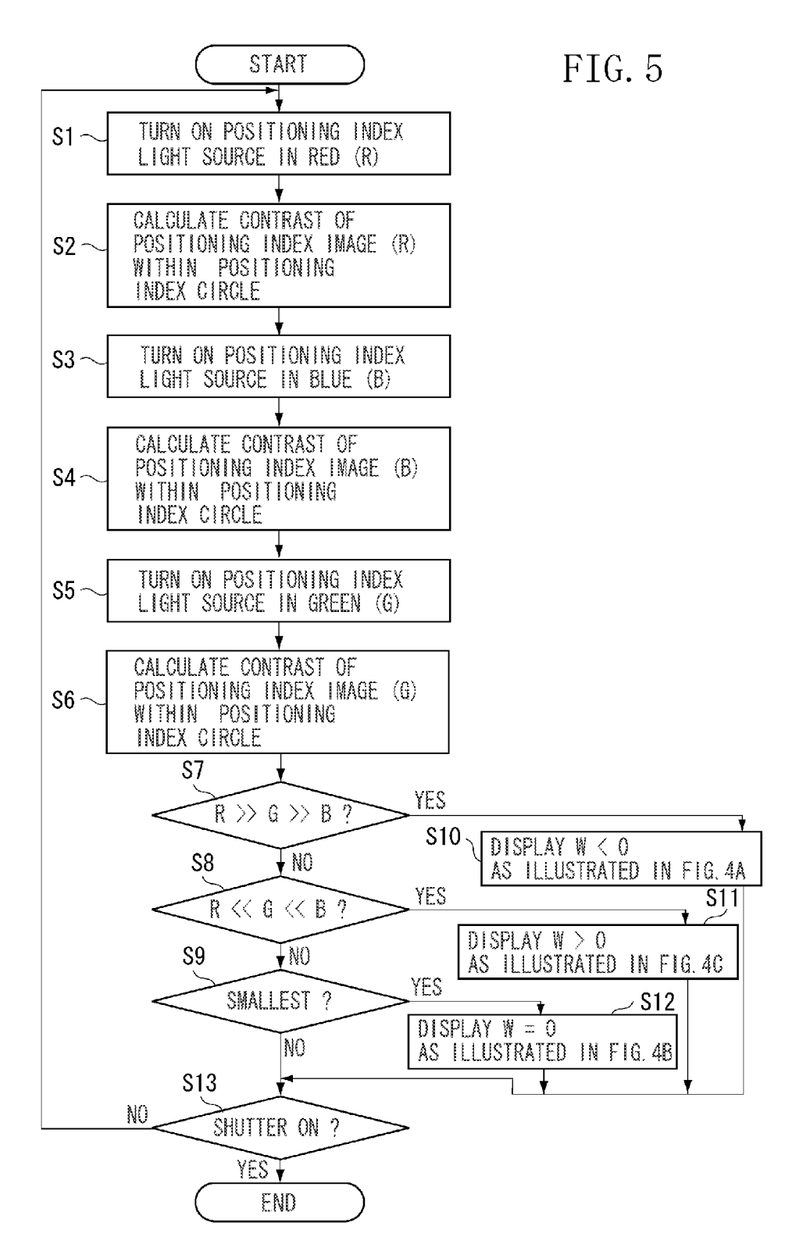
FIG. 5 is a flow chart illustrating operations according to the first exemplary embodiment.

FIG. 5 is a flow chart of operations of the calculation unit 22. The calculation unit 22 selects wavelength ranges of the positioning index light source 15 to sequentially turn on the positioning index light source 15 in red (R), blue (B), and green (G). Subsequently, the cornea Ec of the subject's eye E reflects light, and the image sensor 13a forms the positioning index images A. Next, the image sensor 13a supplies the image data to the calculation unit 22 via the image signal processing unit 21.

In step S1, the calculation unit 22 turns on the positioning index light source 15 in red (R). In step S2, the calculation unit 22 uses, as positional gap information, the image data on the positioning index images A in red (R) supplied from the image signal processing unit 21, to calculate the contrast of each of the positioning index images A in the positioning index circles C illustrated in FIGS. 4A to 4C. In step S3, the calculation unit 22 turns on the positioning index light source 15 in blue (B). In step S4, the calculation unit 22 uses the image data on the positioning index images A in blue (B) supplied from the image signal processing unit 21, to calculate the contrast of each of the positioning index images A in the positioning index circles C illustrated in FIGS. 4A to 4C.

In step S5, the calculation unit 22 turns on the positioning index light source 15 in green (G). In step S6, the calculation unit 22 uses the image data on the positioning index images A in green (G) supplied from the image signal processing unit 21, to calculate the contrast of each of the positioning index images A in the positioning index circles C illustrated in FIGS. 4A to 4C. Since correctly positioned vertically and horizontally, each of the positioning index images A is located in one of the positioning index circles C illustrated in FIGS. 4A to 4C.

Figure 6:
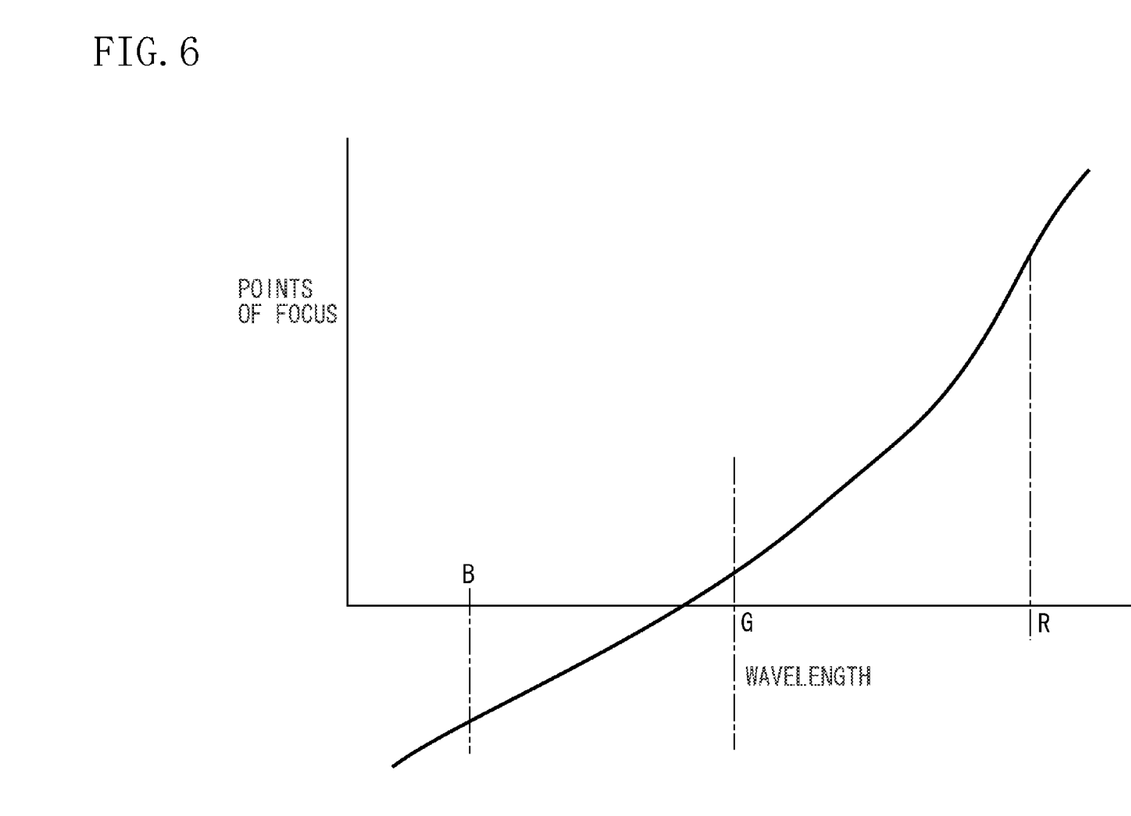
FIG. 6 is a graph illustrating points of focus over wavelengths.

As illustrated in FIG. 6, the axial chromatic aberration causes points of focus to vary for each of the wavelengths red (R), green (G), and blue (B) of the LEDs of the positioning index light source 15. In the first exemplary embodiment, the projection surface of the optical fiber 14 is arranged so that, when the positioning index light source 15 is turned on in green (G), the positioning index images A are focused.

Figure 7:
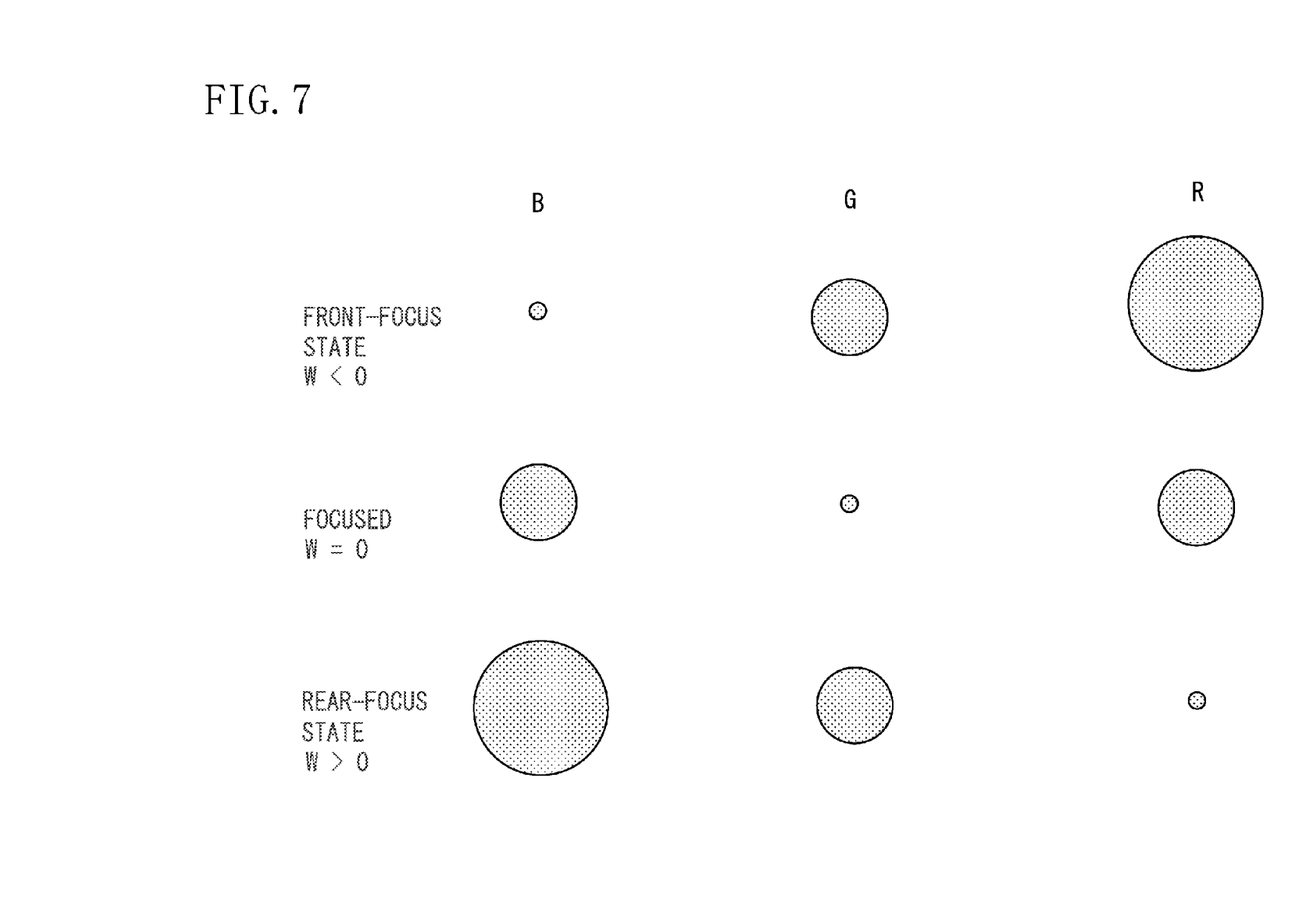
FIG. 7 illustrates blurs of positioning index images when the positioning index light source is turned on, in red (R), green (G), and blue (B) and indicates positions of the fundus camera with respect to an appropriate position.

Thus, as illustrated in FIG. 7, when the fundus camera is positioned on the same side as the subject's eye E relative to the appropriate position, namely, when the fundus camera is in a front-focus state (W<0), the positioning index light source 15 that is turned on in blue (B) produces most-focused positioning index images A. The positioning index light sources 15 in green (G) and in red (R) produce more-blurred and most-blurred positioning index images A, respectively.

In contrast, when the fundus camera is positioned on the opposite side of the subject's eye E relative to the appropriate position, namely, when the fundus camera is in a rear-focus state (W>0), the positioning index light source 15 that is turned on in red (R) produces most-focused positioning index images A. The positioning index light sources 15 in green (G) and in blue (B) produce more-blurred and most-blurred positioning index images A, respectively. For example, assuming that the relationship B<<G indicates that the positioning index light source 15 that is turned on in blue (B) provides a smaller image and a better contrast compared with the positioning index light source 15 that is turned on in green (G), when W<0, R>>G>>B, when W>0, R<<G<<B, and when W=0, the positioning index light source 15 that is turned on in green (G) provides the best contrast.

Thus, based on the blur of each of the positioning index images A in red (R), green (G), and blue (B) reflected by the cornea Ec, the calculation unit 22 calculates characteristics of the index images, including an appropriate direction in moving the fundus camera body part (either closer to or farther away from the subject's eye E). The calculation unit 22 detects positional gap information and allows the display unit 23 to display the information.

In step S7, if the calculation unit 22 determines the relationship R>>G>>B (YES in step S7), the operation proceeds to step S10. In step S10, since the working distance is represented as W<0, the display unit 23 displays: the fundus image Er'; the positioning index images A; a figure F showing a positional relationship between the appropriate position, the current position of the fundus camera, and the position of the subject's eye E; and an appropriate direction in moving the fundus camera body part, as illustrated in FIG. 4A.

In step S8, if the calculation unit 22 determines the relationship R<<G<<B (YES in step S8), the operation proceeds to step S11. In step S11, since the working distance is represented as W>0, the display unit 23 displays: the fundus image Er'; the positioning index images A; a figure F showing a positional relationship between the appropriate position, the current position of the fundus camera, and the position of the subject's eye E; and an appropriate direction in moving the fundus camera body part, as illustrated in FIG. 4C.

In step S9, if the calculation unit 22 determines that the positioning index images A in green (G) have the best contrast (YES in step S9), the operation proceeds to step S12. In step S12, since the working distance is represented as W=0 (focused), the display unit 23 displays: the fundus image Er'; the positioning index images A; a figure F showing a positional relationship between the fundus camera at the appropriate position and the position of the subject's eye E; and an appropriate direction in moving the fundus camera body part, as illustrated in FIG. 4B.

In step S13, if the operator presses a shutter on the input unit 28, the calculation unit 22 ends a series of positioning operations and starts an image-capturing operation. These operations in steps S1 to S13 are repeated until the operator presses the shutter on the input unit 28. The operator adjusts the working distance based on the direction of the arrow displayed on the display unit 23, that is, in an appropriate direction.

The operator observes the images formed by the focus index 6d and displayed on the display unit 23 and controls a focus knob (not illustrated) to align the right and left focus index images formed by the focus split prism. In this way, the fundus Er and the focus index 6d are optically brought in a conjugate relation with each other. Since the focus link mechanism 16 controls the focus index 6d of the focus index projection unit 6 and the image sensor 13a to be in an optically conjugate relation, the fundus Er and the image sensor 13a are optically brought in a conjugate relation, and therefore, the fundus Er can be focused.

When the calculation unit 22 detects that the operator has pressed the shutter on the input unit 28, the calculation unit 22 starts an image-capturing operation. Namely, the calculation unit 22 drives the drive circuit 27 to turn off the positioning index light source 15 and drives the drive circuit 26 to move the focus index projection unit 6 in direction B, which is thereby retracted from the optical path O1. In addition, the calculation unit 22 inserts the quick-return mirror 4 in the optical path O1 and drives the drive circuit 25 to cause the imaging light source 9 to emit light. When alignment and focus adjustment are completed, the right and left bars of the focus adjustment index P are aligned and each of the positioning index images A is positioned in one of the positioning index circles C, as illustrated in FIG. 4B.

The luminous flux emitted from the imaging light source 9 passes through the diaphragm 10 having a ring aperture, and the quick-return mirror 4 reflects the luminous flux. Subsequently, the luminous flux takes the same path as the luminous flux emitted from the observation light source 1 and illuminates the fundus Er. Next, the fundus Er reflects the luminous flux and the image sensor 13a forms the fundus image Er'. The image sensor 13a executes a photoelectric conversion, and the image signal processing unit 21 reads the converted data and generates digital fundus still image data. Simultaneously, the display unit 23 displays the image data, and the recording unit 29 receives the image data via the calculation unit 22 to record the image data. Since the imaging light source 9 outputs light of wavelengths of all visible light ranges, the image signal processing unit 21 generates color fundus image data.

According to the first exemplary embodiment, the positioning index light source 15 includes tricolor LEDs and is capable of emitting light of three colors of red (R), green (G), and blue (B). However, if it is only necessary to detect an appropriate direction to move the fundus camera, more specifically, whether to move the fundus camera closer to or farther away from the subject's eye E, two of the three colors red (R), green (G), and blue (B) may be used.

Figure 8:
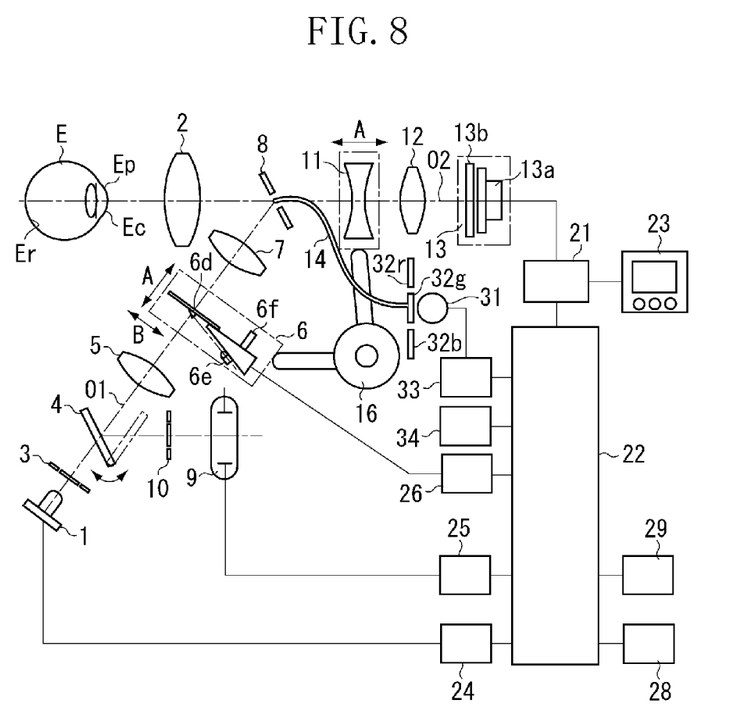
FIG. 8 illustrates a configuration of a fundus camera according to a second exemplary embodiment.

FIG. 8 illustrates a configuration of a fundus camera according to a second exemplary embodiment, and in FIGS. 1 and 8, same reference characters denote same elements. While the fundus camera according to the first exemplary embodiment includes the positioning index light source 15 including tricolor LEDs, the fundus camera according to the second exemplary embodiment includes a positioning index light source 31 configured to emit white light. Further, the fundus camera includes color filters 32r, 32g, and 32b that only transmit red (R), green (G), and blue (B), respectively, in front of the positioning index light source 31. The fundus camera further includes a drive unit 33 configured to drive the positioning index light source 31 and a drive unit 34 configured to drive the color filters 32r, 32g, and 32b.

While the fundus camera according to the first exemplary embodiment turns on each of the red (R), green (G), and blue (B) LEDs, the fundus camera according to the second exemplary embodiment controls the drive unit 34 to selectively insert the color filter 32r, 32g, or 32b between the positioning index light source 31 and the optical fiber 14. In this way, the fundus camera according to the second exemplary embodiment can operate in the same way as that according to the first exemplary embodiment in which the calculation unit 22 selectively turns on the positioning index light source 15 in red (R), green (G), or blue (B).

Figure 9:
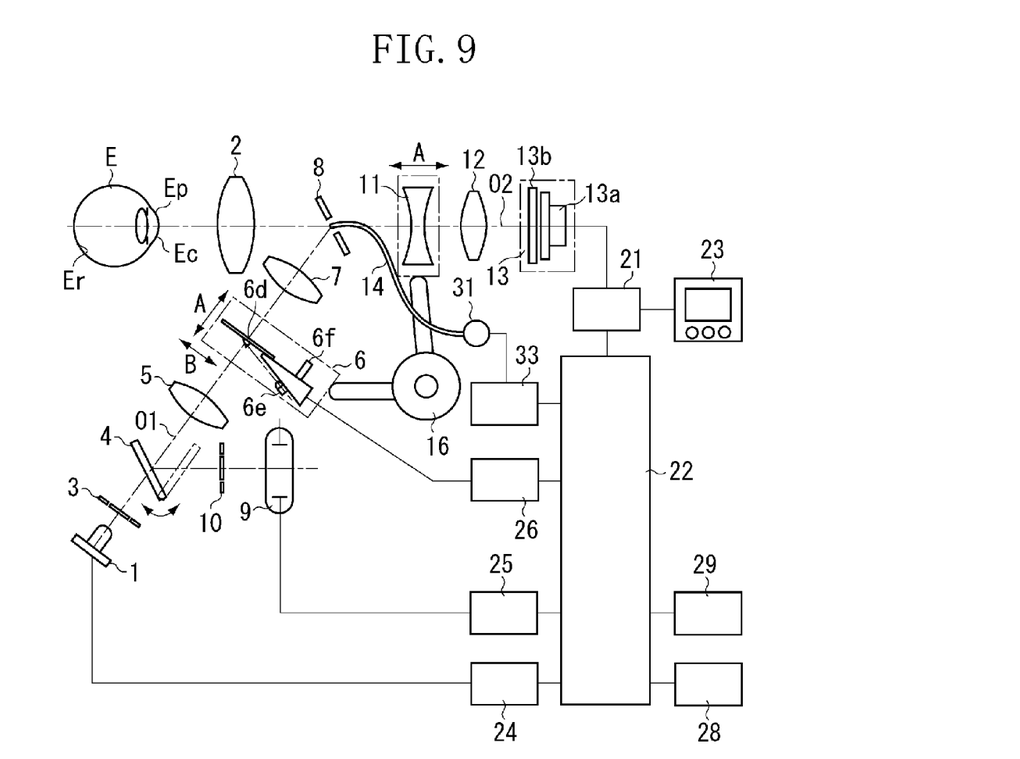
FIG. 9 illustrates a configuration of a fundus camera according to a third exemplary embodiment.
Figure 10:
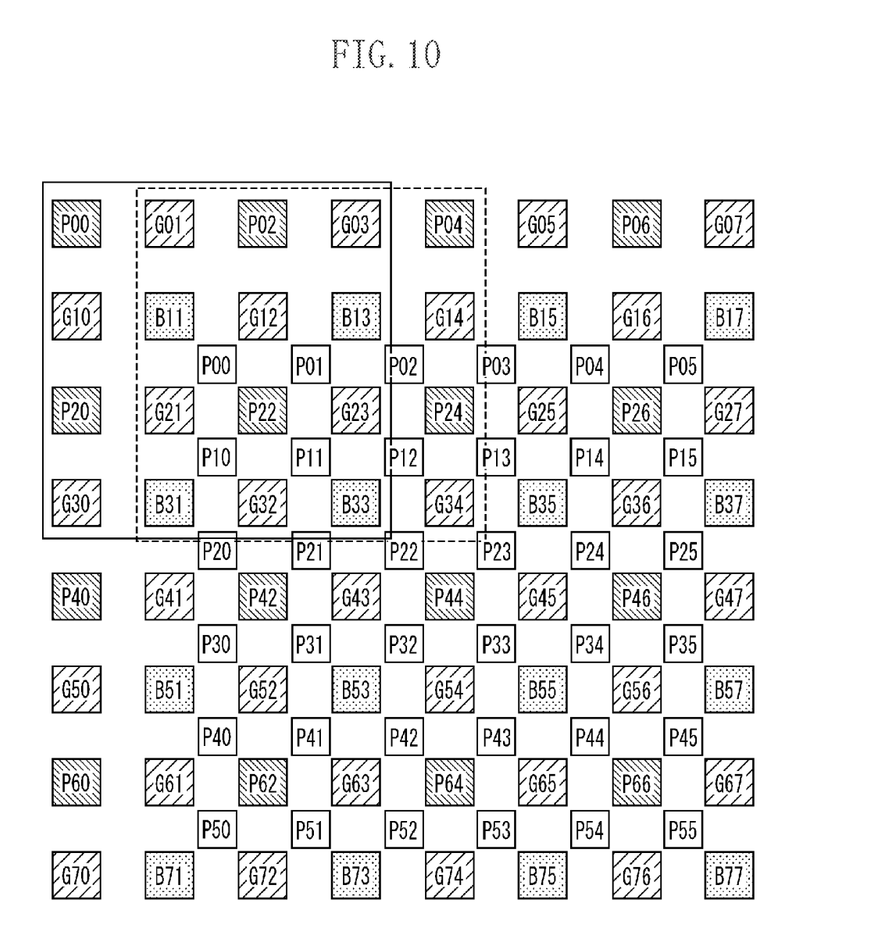
FIG. 10 illustrates filters of a tricolor wavelength separation unit.

FIG. 9 illustrates a configuration of a fundus camera according to a third exemplary embodiment, and in FIGS. 1, 8 and 9, same reference characters denote same elements. As described above, the fundus camera includes the tricolor wavelength separation unit 13b in front of the image sensor 13a in the imaging unit 13. The tricolor wavelength separation unit 13b includes tricolor filters of red (R), green (G), and blue (B) in a mosaic-like pattern corresponding to each pixel of the image sensor 13a, as illustrated in FIG. 10.

The image signal processing unit 21 reads and amplifies each pixel data from the image sensor 13a and calculates virtual pixel values to generate an image. Calculation of a virtual pixel P00 will be hereinafter described. The image signal processing unit 21 calculates the value of each RGB color of the virtual pixel P00 by using light reception data about pixels R00, R02, B11, G12, B13, R20, G21, R22, B31, and B33, among the pixels surrounded by the solid line around the virtual pixel P00.

In the following, P00r, P00g, and P00b denote the values of the individual RGB colors of the virtual pixel P00. The values can be represented by the following equations.

$P00g=(G12+G21)/2$ $P00r=(9\cdot R22+3\cdot R02+3\cdot R20+R00)/16$ $P00b=(9\cdot B11+3\cdot B13+3\cdot B31+B33)/16$ The image signal processing unit 21 calculates a virtual pixel P01, which is positioned on the right side of the virtual pixel P00, by using light reception data about pixels R02, R04, B11, G12, B13, R22, G23, R24, B31, and B33, among the pixels surrounded by the dashed line around the virtual pixel P01.

$P01g=(G12+G23)/2$ $P01r=(9\cdot R22+3\cdot R02+3\cdot R24+R04)/16$ $P01b=(9\cdot B13+3\cdot B11+3\cdot B33+B31)/16$ In this way, the image signal processing unit 21 calculates each virtual pixel value by using light data received in a range of 4×4 pixels around each virtual pixel P to generate an image.

Figure 11:
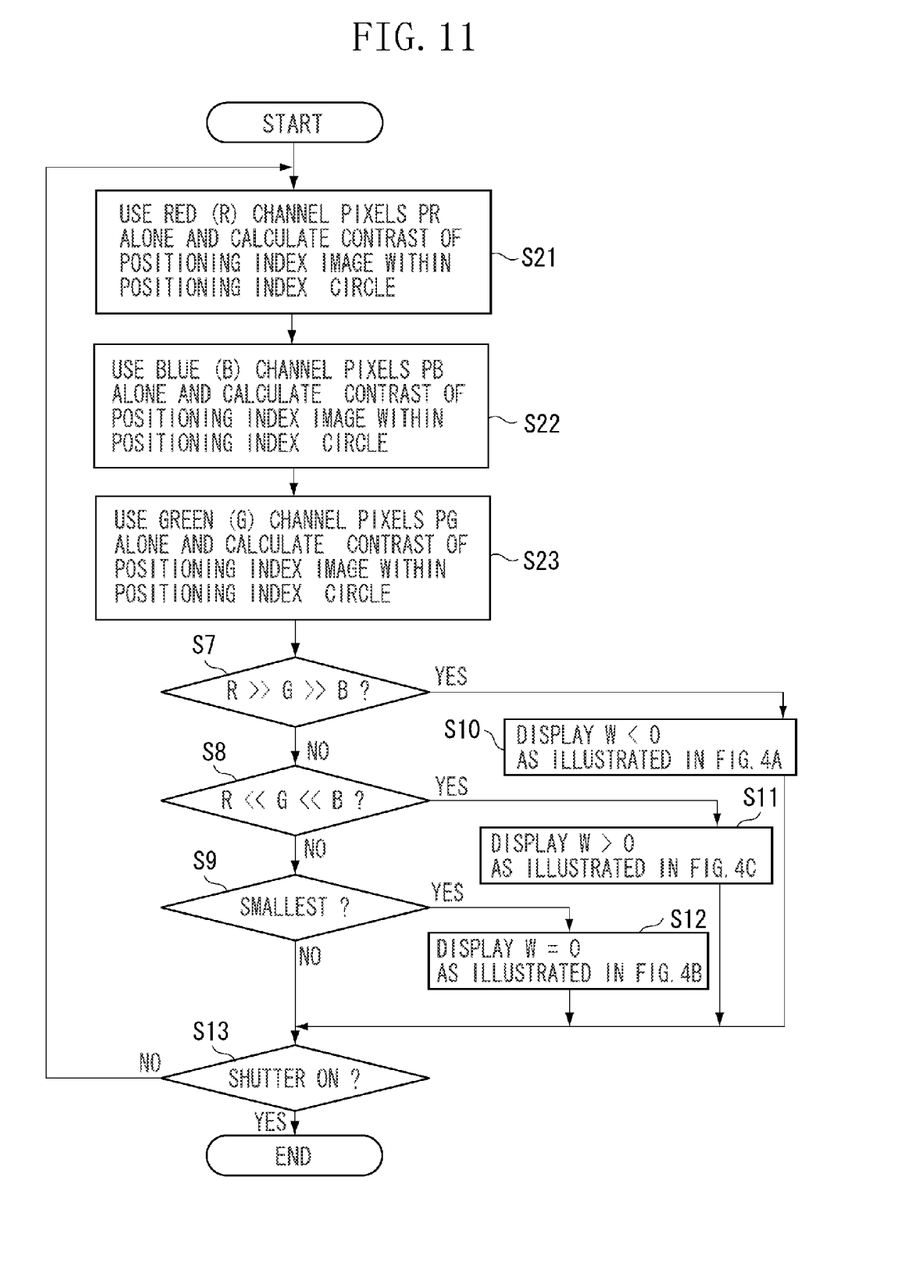
FIG. 11 is a flow chart illustrating operations according to the third exemplary embodiment.

FIG. 11 is a flow chart illustrating operations of the calculation unit 22. When compared with the flow chart of FIG. 5 illustrating operations of the calculation unit 22 according to the first exemplary embodiment, in FIG. 11, steps S1 to S6 of the flow chart of FIG. 5 are replaced with steps S21 to S23.

In step S21, the calculation unit 22 receives image data from the image signal processing unit 21, uses red (R) channel pixels Pr alone, and calculates contrast of each of the positioning index images A in the positioning index circles C illustrated in FIGS. 4A to 4C. In step S22, based on the image data supplied from the image signal processing unit 21, the calculation unit 22 uses blue (B) channel pixels Pb alone, and calculates contrast of each of the positioning index images A in the positioning index circles C illustrated in FIGS. 4A to 4C. In step S23, based on the image data supplied from the image signal processing unit 21, the calculation unit 22 uses green (G) channel pixels Pg alone, and calculates contrast of each of the positioning index images A in the positioning index circles C illustrated in FIGS. 4A to 4C. The operations of steps S7 to S13 are the same as those in the first exemplary embodiment.

Unlike the positioning index light source 15 in the first exemplary embodiment, the positioning index light source 31 does not include a plurality of single-wavelength light sources. However, the positioning index light source 31 is a multiband wavelength light source having spectral sensitivity characteristics of at least two wavelength components among red (R), green (G), and blue (B). After the luminous flux passes through the tricolor wavelength separation unit 13b in the imaging unit 13 and the image sensor 13a forms the positioning index images A, the calculation unit 22 calculates contrast of each of the positioning index images A for each of the channels red (R), green (G), and blue (B). In this way, the calculation unit 22 can determine whether the fundus camera is positioned on the same side or the opposite side of the subject's eye E with respect to an appropriate position.

Figure 12:
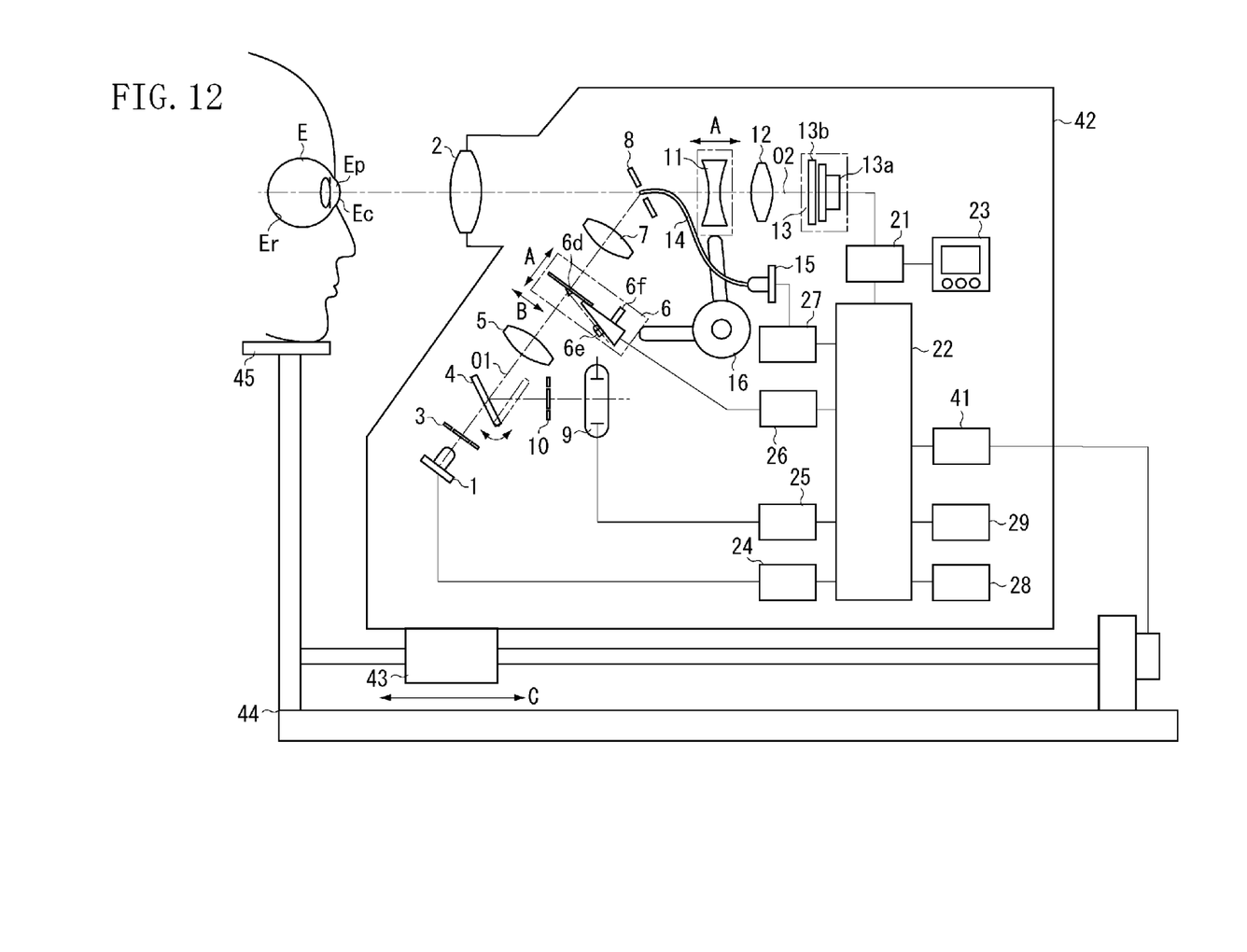
FIG. 12 illustrates a configuration of a fundus camera according to a fourth exemplary embodiment.

FIG. 12 illustrates a configuration of a fundus camera according to a fourth exemplary embodiment, and in FIGS. 1, 8, and 9, same reference characters denote same elements. The fundus camera according to the fourth exemplary embodiment includes a motor driving unit 41 in a fundus camera body part 42, in addition to the configuration of the fundus camera according to the first exemplary embodiment. The motor driving unit 41 is connected to the calculation unit 22 and a motor 43. The body part 42 is held on a base unit 44, and the subject's eye E is fixed on a chin rest 45 of the base unit 44. When the motor 43 rotates, the body part 42 can move in direction C.

The calculation unit 22 turns on the positioning index light source 15 in red (R), blue (B), and green (G) sequentially, the cornea Ec reflects the luminous flux, and the image sensor 13a receives the reflected luminous flux to form the positioning index images A. The image sensor 13a supplies the image data to the calculation unit 22 via the image signal processing unit 21.

According to the fourth exemplary embodiment, the projection surface of the optical fiber 14 is arranged so that, when W=0, the positioning index light source 15 that is turned on in green (G) produces focused positioning index images A. As described above with reference to FIG. 7, when the fundus camera is positioned on the same side as the subject's eye E relative to the appropriate position, namely, when the working distance is represented as W<0, the positioning index light source 15 that is turned on in blue (B) produces most-focused positioning index images A. The positioning index light sources 15 in green (G) and red (R) produce more-blurred and most-blurred positioning index images A, respectively.

Figure 13:
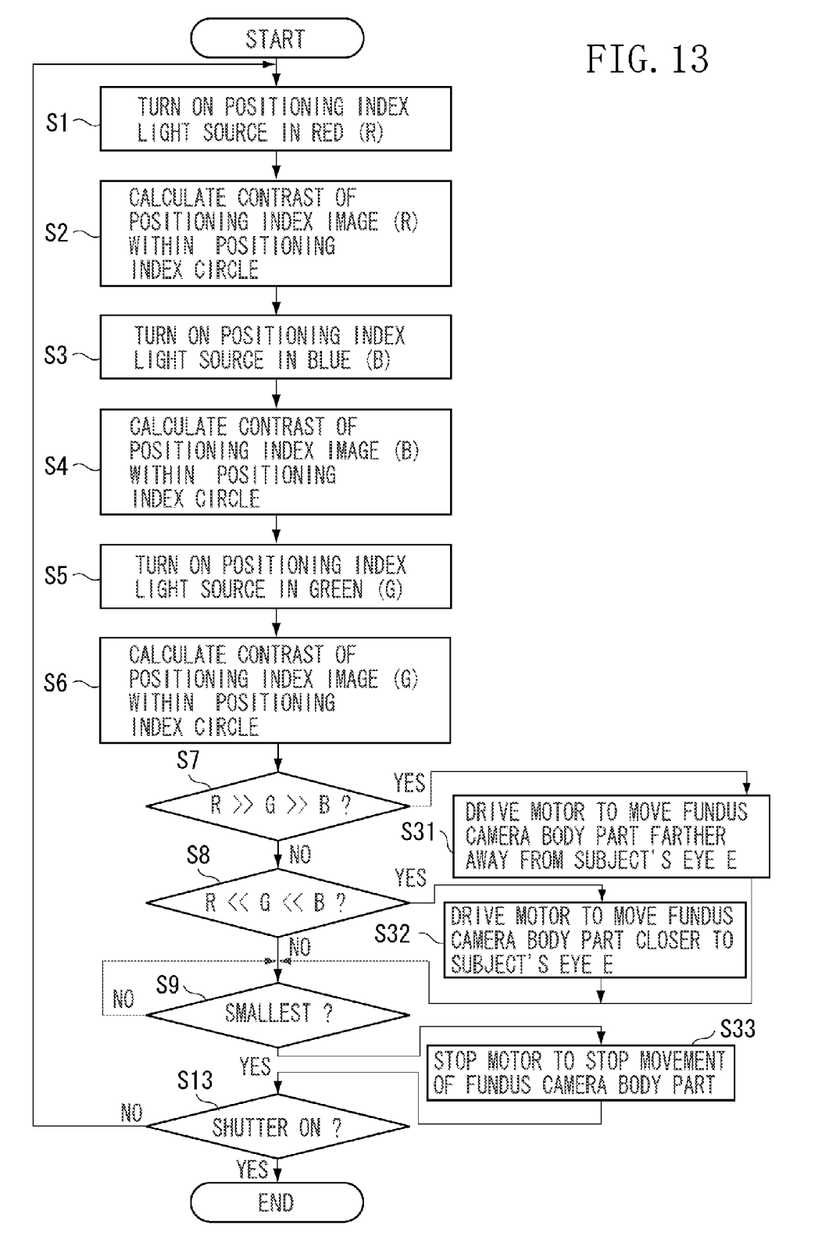
FIG. 13 is a flow chart illustrating operations according to the fourth exemplary embodiment.

FIG. 13 is a flow chart illustrating operations of the calculation unit 22, and this flow chart includes steps S31 to S33, instead of steps S10 to S13 of the flow chart of FIG. 5 according to the first exemplary embodiment. The calculation unit 22 turns on the positioning index light source 15 in red (R), blue (B), and green (G) selectively and sequentially, the cornea Ec reflects the luminous flux, and the image sensor 13a receives the reflected luminous flux to form the positioning index images A. The image sensor 13a supplies the image data to the calculation unit 22 via the image signal processing unit 21. Steps S1 to S6 are the same as those in the flow chart of FIG. 5.

In step S7, if the calculation unit 22 determines R>>G>>B (YES in step S7), the operation proceeds to step S31. Since the fundus camera is positioned on the same side as the subject's eye E relative to an appropriate position (W<0), the calculation unit 22 controls the motor driving unit 41 to drive the motor 43 so that the body part 42 is moved farther away from the subject's eye E.

In step S8, if the calculation unit 22 determines R<<G<<B (YES in step S8), the operation proceeds to step S32. In step S32, since the fundus camera is on the opposite side of the subject's eye E relative to the appropriate position (W>0), the calculation unit 22 drives the motor 43 to move the body part 42 closer to the subject's eye E.

After step S31 or S32, the operation proceeds to step S9, and the calculation unit 22 determines whether the positioning index images A in green (G) have the best contrast. If the calculation unit 22 determines that the positioning index images A in green (G) have the best contrast (YES in step S9), the operation proceeds to step S33. In step S33, the calculation unit 22 stops the motor 43 to stop movement of the fundus camera body part 42. In this way, the fundus camera can automatically move to an appropriate position.

In step S13, if the operator presses the shutter on the input unit 28 (YES in step S13), the calculation unit 22 ends a series of positioning operations and starts an image-capturing operation. The operations in steps S1 to S19 are repeated until the operator presses the shutter and the calculation unit 22 starts an image-capturing operation.

Other Embodiments

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-162825 filed Jul. 9, 2009, which is hereby incorporated by reference herein in its entirety.

What is claimed is:

1. An ophthalmic apparatus comprising:
   an index projection unit configured to project an alignment index on a cornea of a subject's eye;
   an imaging unit configured to capture, as an alignment index image, an image reflected from the subject's eye on which the index projection unit projects the alignment index;
   an acquiring unit configured to acquire contrasts of the alignment index image in a first wavelength range and a second wavelength range different from the first wavelength range among visible ranges that are wavelength ranges of the alignment index projected by the index projection unit; and
   a control unit configured to perform at least one of an operation to change a working distance from a main body part including the index projection unit and the imaging unit to the subject's eye and an operation to cause a display unit to display a display form indicating a direction in which the working distance is to be changed so that a difference between the acquired contrasts becomes small.

2. The ophthalmic apparatus according to claim 1, wherein the index projection unit comprises a plurality of light sources each emitting light in the first and second wavelength ranges, and selectively lights the plurality of light sources.

3. The ophthalmic apparatus according to claim 1, wherein the index projection unit selectively emits luminous fluxes in the first and second wavelength ranges.

4. The ophthalmic apparatus according to claim 1, further comprising:
   a tricolor wavelength separation unit arranged in the imaging unit,
   wherein the acquiring unit acquires a plurality of contrasts based on the separated image data.

5. The ophthalmic apparatus according to claim 1, wherein the index projection unit includes a light source configured to emit light in a visible range and a wavelength selection unit configured to selectively transmit light in at least two wavelength ranges among wavelength ranges of the light emitted from the light source.

6. The ophthalmic apparatus according to claim 1, further comprising:
   an illumination optical system configured to project illumination light on a fundus of a subject's eye; and
   an imaging optical system configured to capture an image reflected from the fundus via an objective lens,
   wherein the index projection unit projects a positioning index as the index on the subject's eye via the objective lens, and
   wherein the imaging unit is arranged in the imaging optical system, and the imaging optical system captures an image of the subject's eye.

7. The ophthalmic apparatus according to claim 1, further comprising:
   a positional gap information detection unit configured to detect information about positional gap between the subject's eye and the imaging optical system relative to an appropriate working distance, based on the characteristics for each of the wavelength ranges; and
   a display unit configured to display the information about positional gap supplied from the positional gap information detection unit.

8. The ophthalmic apparatus according to claim 1, further comprising:
   a positional gap information detection unit configured to detect information about positional gap between the subject's eye and the imaging optical system relative to an appropriate working distance, based on the characteristics for each of the wavelength ranges;
   a control unit configured to position the imaging optical system at an appropriate working distance relative to the subject's eye, based on the information about positional gap supplied from the positional gap information detection unit; and
   a drive unit configured to drive the imaging optical system in a working distance direction, based on a signal from the control unit.

9. An ophthalmic apparatus comprising:
   an acquiring unit configured to acquire contrasts of an image reflected from a subject's eye in a first wavelength range and a second wavelength range different from the first wavelength range among visible ranges that are wavelength ranges of the image reflected from the subject's eye; and a control unit configured to perform at least one of an operation to change a working distance from a main body part including an imaging unit configured to capture an image of the subject's eye to the subject's eye and an operation to cause a display unit to display a display form indicating a direction in which the working distance is to be changed so that a difference between the acquired contrasts becomes small.

10. An ophthalmic method comprising:

acquiring contrasts of an image reflected from a subject's eye in a first wavelength range and a second wavelength range different from the first wavelength range among visible ranges that are wavelength ranges of the image reflected from the subject's eye; and performing at least one of an operation to change a working distance from a main body part including an imaging unit configured to capture an image of the subject's eye to the subject's eye and an operation to cause a display unit to display a display form indicating a direction in which the working distance is to be changed so that a difference between the acquired contrasts becomes small.

11. A program causing a computer to execute the ophthalmic method according to claim 10.

12. The ophthalmic apparatus according to claim 1, wherein the acquiring unit acquires contrasts of the alignment index image in a third wavelength range between the first and the second wavelength ranges among the visible ranges, and wherein the control unit performs at least one of the operation to change the working distance and the operation to cause the display unit to display the display form based on the contrasts of the alignment index image in the third wavelength range.

13. The ophthalmic apparatus according to claim 12, wherein the control unit stops changing the working distance based on the characteristics of the index image in the third wavelength range when the control unit performs the operation to change the working distance.

14. The ophthalmic apparatus according to claim 12, wherein the first wavelength range is approximately at one end of the visible ranges and the second wavelength range is approximately at the other end of the visible ranges, and wherein the third wavelength range is approximately in the center of the visible wavelength ranges.

15. The ophthalmic apparatus according to claim 12, wherein the first and the second wavelength ranges are red and blue wavelength ranges, and wherein the third wavelength range is a green wavelength range.

16. An ophthalmic method comprising:

projecting an alignment index on a cornea of a subject's eye;

capturing, as an alignment index image, an image reflected from the subject's eye on which the alignment index is projected;

acquiring contrasts of the alignment index image in a first wavelength range and a second wavelength range different from the first wavelength range among visible ranges that are wavelength ranges of the projected alignment index; and performing at least one of an operation to change a working distance from a main body part including an index projection unit and an imaging unit to the subject's eye and an operation to cause a display unit to display a display form indicating a direction in which the working distance is to be changed so that a difference between the acquired contrasts becomes small.

17. A program causing a computer to execute the ophthalmic method according to claim 16.

18. The ophthalmic method according to claim 16, further comprising:

acquiring contrasts of the alignment index image in a third wavelength range between the first and the second wavelength ranges among the visible ranges; and performing at least one of the operation to change the working distance and the operation to cause the display unit to display the display form based on the contrasts of the alignment index image in the third wavelength range.

19. The ophthalmic apparatus according to claim 12, wherein the control unit is configured to perform at least one of the operation to change the working distance and the operation to cause the display unit to display the display form so that contrasts of the alignment index image in the third wavelength range becomes best.

20. The ophthalmic method according to claim 16, wherein at least one of the operation to change the working distance and the operation to cause the display unit to display the display form is performed so that contrasts of the alignment index image in the third wavelength range becomes best.

21. The ophthalmic apparatus according to claim 1, wherein, in a case where the first wavelength range is longer than the second wavelength range, the control unit is configured to perform at least one of the operation to change the working distance and the operation to cause the display unit to display the display form, so that the main body part is moved closer to the subject's eye when contrasts of the first wavelength range are better than contrasts of the second wavelength range, and so that the main body part is moved farther from the subject's eye when contrasts of the first wavelength range are not better than contrasts of the second wavelength range.

22. The ophthalmic method according to claim 16, wherein, in a case where the first wavelength range is longer than the second wavelength range, at least one of the operation to change the working distance and the operation to cause the display unit to display the display form is performed in the performing, so that the main body part is moved closer to the subject's eye when contrasts of the first wavelength range are better than contrasts of the second wavelength range, and so that the main body part is moved farther from the subject's eye when contrasts of the first wavelength range are not better than contrasts of the second wavelength range.

* * * * *